United States Patent
Berry

(10) Patent No.: US 8,319,195 B2
(45) Date of Patent: Nov. 27, 2012

(54) METHODS AND APPARATUS FOR STERILIZATION OF AIR AND OBJECTS

(75) Inventor: Lambert Darryl Berry, Hawthorne, NV (US); John Robert Berry, legal representative, Coronado, CA (US)

(73) Assignee: Safe Haven, Inc., Hawthorne, NV (US)

( * ) Notice: Subject to any disclaimer, the term of this patent is extended or adjusted under 35 U.S.C. 154(b) by 0 days.

(21) Appl. No.: 13/249,035

(22) Filed: Sep. 29, 2011

(65) Prior Publication Data

US 2012/0074335 A1 Mar. 29, 2012

Related U.S. Application Data

(63) Continuation of application No. 11/302,179, filed on Dec. 12, 2005, now abandoned, which is a continuation-in-part of application No. PCT/US2004/018772, filed on Jun. 14, 2004, which is a continuation of application No. 10/640,477, filed on Aug. 11, 2003, now abandoned.

(60) Provisional application No. 60/478,231, filed on Jun. 12, 2003.

(51) Int. Cl.
*B01D 17/06* (2006.01)
*G01N 23/00* (2006.01)

(52) U.S. Cl. ............. 250/455.11; 210/748; 55/DIG. 30; 204/660

(58) Field of Classification Search .................. 422/1, 5, 422/22, 24, 186; 250/455.11; 210/748; 55/DIG. 30; 204/660
See application file for complete search history.

(56) References Cited

U.S. PATENT DOCUMENTS

| 3,642,353 | A | | 2/1972 | Field |
| 3,817,703 | A | | 6/1974 | Atwood |
| 3,941,670 | A | | 3/1976 | Pratt, Jr. |
| 3,955,921 | A | | 5/1976 | Tensmeyer |
| 4,011,456 | A | | 3/1977 | Bredewater et al. |
| 4,042,325 | A | | 8/1977 | Tensmeyer |
| 4,115,280 | A | * | 9/1978 | Pratt, Jr. ............... 422/186.1 |
| 4,226,369 | A | | 10/1980 | Botts et al. |
| 4,397,823 | A | | 8/1983 | Dimpfl |
| 4,529,489 | A | | 7/1985 | McDonald et al. |
| 4,613,277 | A | | 9/1986 | Guay |
| 4,621,195 | A | | 11/1986 | Larsson |
| 4,680,771 | A | | 7/1987 | Koseki |
| 4,806,768 | A | | 2/1989 | Keutenedjian |

(Continued)

FOREIGN PATENT DOCUMENTS

WO    WO 98/58842    12/1998

(Continued)

*Primary Examiner* — Jill Warden
*Assistant Examiner* — Monzer Chorbaji
(74) *Attorney, Agent, or Firm* — Knobbe Martens Olson & Bear LLP

(57) ABSTRACT

A portable air sterilization apparatus includes a portable chamber forming an interior volume, a portable source for producing a single beam of collimated light energy, and a rotating beam redirector. The portable chamber includes a first end for introducing air into the chamber, a second end for permitting air to exit from the chamber, a transparent orifice through which a single beam of collimated light energy can be introduced into the interior volume of the chamber; and at least one reflective wall. The rotating beam redirector is adapted to rotate through a complete revolution about a rotational axis and to redirect the single beam of collimated light energy within the chamber during said revolution.

23 Claims, 4 Drawing Sheets

U.S. PATENT DOCUMENTS

| | | | |
|---|---|---|---|
| 4,940,519 A | 7/1990 | Dames | |
| 5,039,495 A | 8/1991 | Kutner et al. | |
| 5,126,020 A | 6/1992 | Dames | |
| 5,250,258 A | 10/1993 | Oh | |
| 5,323,413 A | 6/1994 | Gergely et al. | |
| 5,512,244 A | 4/1996 | Griffiths et al. | |
| 5,557,109 A | 9/1996 | Bidnyy et al. | |
| 5,589,132 A | 12/1996 | Zippel | |
| 5,632,955 A | 5/1997 | Gabbai | |
| 5,650,549 A | 7/1997 | Dellinger et al. | |
| 5,744,094 A | 4/1998 | Castberg et al. | |
| 5,770,785 A | 6/1998 | Tamura et al. | |
| 5,787,144 A | 7/1998 | Findlay | |
| 5,824,277 A | 10/1998 | Campos et al. | |
| 5,832,361 A | 11/1998 | Foret | |
| 5,881,534 A | 3/1999 | Ahlqvist et al. | |
| 6,013,070 A | 1/2000 | Liu et al. | |
| 6,159,422 A | 12/2000 | Graves et al. | |
| 6,248,216 B1 | 6/2001 | Bi et al. | |
| 6,468,433 B1 * | 10/2002 | Tribelski | 210/748.06 |
| 6,508,989 B1 | 1/2003 | Urrusti et al. | |
| 6,555,011 B1 | 4/2003 | Tribelsky et al. | |
| 6,590,217 B1 | 7/2003 | Freeman et al. | |
| 6,646,241 B1 | 11/2003 | Varma et al. | |
| 6,670,726 B2 | 12/2003 | Lee et al. | |
| 6,673,137 B1 | 1/2004 | Wen | |
| 6,730,141 B2 | 5/2004 | Geobel et al. | |
| 6,863,864 B1 | 3/2005 | Ingemanson | |
| 7,373,254 B2 | 5/2008 | Pierce | |
| 7,634,996 B2 | 12/2009 | Gaska et al. | |
| 2002/0085946 A1 | 7/2002 | Suda et al. | |
| 2003/0183503 A1 | 10/2003 | Fujii | |
| 2003/0211005 A1 | 11/2003 | Sloan et al. | |
| 2004/0228756 A1 | 11/2004 | Berry | |
| 2005/0129570 A1 | 6/2005 | Matsuda | |
| 2007/0102280 A1 | 5/2007 | Hunter | |
| 2007/0280851 A1 | 12/2007 | Freeman | |
| 2008/0213128 A1 | 9/2008 | Rudy | |
| 2008/0299002 A1 | 12/2008 | Freeman | |
| 2011/0058982 A1 | 3/2011 | Kaneko | |

FOREIGN PATENT DOCUMENTS

| | | |
|---|---|---|
| WO | WO 99/27970 | 6/1999 |
| WO | WO 2009/139304 | 11/2009 |

* cited by examiner

METHODS AND APPARATUS FOR STERILIZATION OF AIR AND OBJECTS

CROSS-REFERENCE TO RELATED APPLICATIONS

This application is a continuation of U.S. patent application Ser. No. 11/302,179 filed 12 Dec. 2005, which is a continuation-in-part application that claims priority benefit of International Application PCT/US2004/018772 filed on 14 Jun. 2004, designating the United States, which claims priority benefits to U.S. Provisional Patent Application No. 60/478,231, filed 12 Jun. 2003 and U.S. patent application Ser. No. 10/640,477 filed 11 Aug. 2003. The entire disclosures of the aforementioned priority documents are hereby incorporated herein by reference.

BACKGROUND OF THE INVENTION

Description of the Related Art

Sterilization of air and objects has been a common requirement for environments having such requirements. For example, both aspects are required for hospital surgical rooms. The practice of dentistry usually does not require a sterile environment, but it does require the use of sterile dental tools. The state of the art discloses numerous devices and methods for achieving these objectives. However, the inventions of the prior art are limited to fixed installations, and are not considered portable nor adapted to use for object sterilization regimens.

Recent world developments and increased concern over biological weapons has created a need for field deployable structures that provide a safe heaven from biological pathogens as well as aerosols and suspended particulates. Conventional technology is directed primarily towards filtration methods for removing the above-noted micro objects. However, filtration has its limits: cost, size, efficacy, etc.

Another environment that requires filtration in a sealable environment are aircraft in general, and commercial pressurized aircraft in particular. In this environment, a significant percentage of the cabin and cockpit air is recycled. Biological pathogens as well as aerosols and suspended particulates should be removed or reduced in order to minimize the effects of these micro-objects on passengers and professional staff. However, the filtration units on most aircraft do not provide the optimal level of filtration, and it is common to be exposed to undesirable micro-objects, e.g., bacterial or viruses, from either interior sources or exterior sources.

Object sterilization has been primarily limited to use of heat and optionally pressure to sterilize objects, particularly for use in surgical environments. The tools subject to such sterilization fortunately are tolerant of the sterilization environment, however, the sterilization environment limits the type of tools that may be used for surgical procedures. As noted above, the prior art with respect to laser sterilization has been primarily directed to the sterilization of mediums within enclosed vessels, as opposed to the sterilization of objects within the vessel.

SUMMARY OF THE INVENTION

The invention is directed to methods and apparatus for sterilization of air and objects using collimated light of proscribed frequencies (wavelengths), energy densities and durations. The methods broadly encompass directing at least one beam, and in larger applications of embodiments of the invention beams from multiple discrete sources, emitted from a laser or equivalent source of non-ionizing collimated electromagnetic radiation towards a target volume and irradiating the volume for a sufficient period. The duration of radiation exposure depends, in part, upon the residency period of objects within the volume, the intensity and/or energy density of the radiation, the frequency or frequencies of the radiation, and other variables that will be described in more detail below.

In one series of embodiments, the invention is optimized to affect relatively small objects suspended in an air stream. Throughout this patent, this embodiment is referenced as an air sterilization apparatus. These relatively small objects comprise microbes, viruses, particulates, and other micro-objects. The air sterilization apparatus comprises a chamber having an inlet end and an outlet end wherein air is introduced into the chamber at the inlet end and is permitted to exit therefrom through the outlet end. The chamber also defines a substantially transparent orifice through which at least one beam of collimated electromagnetic radiation can pass into the chamber. The orifice may be an opening or may be an opening fitted with a material substantially transparent to the at least one beam.

The chamber further has an interior surface, which may be curvilinear, rectilinear or combinations thereof. Furthermore, a portion or the entire interior surface may have various characteristics including highly reflective properties, surface undulations (linear or curvilinear) or features to assist in beam scattering or intended beam redirection. Moreover, the interior surface may be rigid or flexible. If flexible, the surface may be acted upon by a force (mechanical, electrical or pneumatic) to cause deflection thereof. In certain embodiments, the deflection is cyclical and characterized as a vibration. Optional optical baffles prevent continued propagation of beam energy outside the confines of the chamber, or may be positioned within the functional portion of the chamber to increase distribution of radiation energy and/or modify air transport characteristics.

The at least one beam of collimated electromagnetic radiation is characterized as having at least one discrete frequency or wavelength and preferably a plurality of wavelengths chosen to have particular efficacy at neutralizing the suspended micro-objects. The plurality of discrete wavelength ranges may be serially delivered to the chamber or may be simultaneously delivered. Neutralization includes destruction of the micro-object, functional disruption of the micro-object (as used herein, function disruption has particular applicability to rendering pathogens inactive or substantially biologically harmless), and vaporization of the micro-object. As used herein, "discrete wavelength" refers to a single wavelength and adjacent wavelengths within a small range thereof, e.g., those within about 1% of the primary wavelength.

The introduced at least one beam of collimated electromagnetic radiation can be a single beam of energy. In such an embodiment, the energy density of the beam can be diffused throughout the chamber by modifying the interior surface of the chamber to effect the desired beam diffusion or redirection. Alternatively, the introduced at least one beam of collimated electromagnetic radiation can be multiple beams of energy. In such an embodiment, a single beam is either divided into a plurality of beams prior to entering the chamber, with each beam having a unique angle of incidence when entering the chamber, or a single beam is optically redirected prior to entering the chamber such that each beam redirection results in the entering beam has a unique angle of incidence when entering the chamber. The former can be accomplished by passing the beam through a beam splitter or diffractive element, while the later can be accomplished by passing the beam through or reflecting the beam off a movable element. Alternative means for distributing the at least one beam include selectively removing the cladding from a fiber optic or periphery of a light pipe to permit partial escapement of any energy within the fiber or light pipe. Those persons skilled in the art will appreciate that the geometry of such material removal will create unique dispersion characteristics that may be matched to the particular environment in which the dispersion is desired.

The source of the at least one beam of collimated electromagnetic radiation is preferably a laser having a power output sufficient for achieving the intended purpose of the apparatus and methods. The laser may be of the continuous wave or pulsed type, with many preferred embodiments employing a pulsed type for reasons well known to those skilled in the art. Depending upon the energy density for a given application, a 10 watt $CO_2$ laser emitting radiation in the infrared region may be sufficient, or higher power and/or additional lasers may be employed. Again, the wavelength of the laser or ultimately emitted beam(s) is selected based upon the target species identified for neutralization.

To ensure that air having exited the air sterilization apparatus has been appropriately treated, various embodiments of this series may employ a particulate matter feedback arrangement. The feedback arrangement preferably comprises a backscatter detector operatively exposed to the air stream during or after treatment by the invention, and to either a portion of the at least one beam of collimated electromagnetic radiation or a separate source such as an optical wavelength laser. The detector, commonly at least one photovoltaic element, is positioned to either receive backscattered light or transmitted light, depending upon the mode of implementation, created by the interaction of suspended matter in the air stream with the radiation. By transforming the modulated signal output of the detector into discernable data, a determination can be made regarding the efficacy of the air sterilization apparatus for the parameters being employed. If, for example, the resulting data indicates an unacceptably high level of suspended matter exists, or if the feedback arrangement can discern particle characteristics and such data indicate the presence of undesired matter, the operational parameters of the apparatus can be modified to address the undesired conditions. Such adjustable parameters may be the air stream velocity which affects the residency of an air mass within the apparatus, the intensity or energy density of the at least one beam, pulse width of the at least one beam if variable, beam scattering parameters and so on. In addition or alternatively thereto, an air stream redirector or damper can be activated to return the undesired air stream back to the input of the apparatus for further treatment, this option being employed when the feedback arrangement is located after the exposure cavity of the apparatus.

In certain embodiments of this series, the air sterilization apparatus is portable, i.e., not integrated with or part of a permanent or semi-permanent structure (non-deployable assets). In these embodiments, the apparatus may further comprise an air handler, e.g., a blower having an air displacement element and a motor, and the outlet of the chamber is adapted to fluidly couple with a portable structure such as a container or other transportable rigid structure, or couple with erectable structures such as hazardous materials tents, field medical tents and related medical temporary structures, neonatal care tents, burn recovery tents, and other inflatable tents. Preferably, either type of structure is relatively sealable from an external environment whereby the apparatus provides sterilized air to the interior of the structure and further creates/maintains some level of positive pressure within the structure relative to the environment's atmospheric pressure adjacent to the structure, thus minimizing the undesirable ingress of unconditioned air. The apparatus can be discrete from the structure whereby only a duct or similar air transport conduit is used to operative link the apparatus to the structure, or the apparatus can be integrated with the structure whereby the outlet of the chamber is directly exposed to the interior space of the structure. The optional air handler can be located either upstream or downstream of the apparatus, depending upon design considerations.

With respect to portable air sterilization apparatus, it may be desirable to have the apparatus operate off grid. In these embodiments, the apparatus further comprises a power source. The power source may comprise a power generator utilizing an internal or external combustion engine to provide mechanical energy to a suitable electrical generator, the power source may be a battery (rechargeable or not), or the power source may be a fuel cell. For critical applications such as military or first responder environments, fuel cells provide a convenient and reliable means for providing the necessary power to operate even high power lasers and optionally air handlers.

In certain embodiments of this series, the apparatus is integrated into vehicle platforms such as land vehicles, water craft and aircraft. These vehicle platforms are chosen due to their intrinsically controlled internal environment. Using an aircraft platform as an example, the air sterilization apparatus is placed preferably downstream of any air conditioning packs that may be present on the aircraft, otherwise as close to the external air intake(s) as possible. The chamber inlet end and outlet end are operative coupled to the main air flow such that all air to be delivered to the interior areas of the aircraft, e.g., cabin and cockpit, must necessarily pass through the apparatus. Power for the apparatus is obtained from the aircraft power harness, taking into account obvious requirements for voltage and load matching. Upon activation of the apparatus, all air being delivered to the interior areas of the aircraft is subjected to sterilization. Moreover, if intelligently integrated into the aircraft environmental controls, recirculated air is also subjected to re-sterilization thereby addressing issues of contamination originating from within the interior areas of the aircraft. Similar integration approaches can be taken with respect to other vehicle platforms, however, only those with controlled environments will particularly benefit from the sterilization benefits of the apparatus.

In another series of embodiments, the invention is optimized to affect relatively large objects suspended in a chamber. Throughout this patent, this embodiment is referenced as an object sterilization apparatus. The object sterilization apparatus comprises a chamber having a sealable orifice wherein objects of interest can be introduced and removed by a user. Disposed in the chamber are means for temporarily positioning the object(s) to be sterilized in the chamber. The chamber also defines a window through which at least one beam of collimated electromagnetic radiation can pass into the chamber. The window may be an opening or preferably may be an opening in which a material substantially transparent to the at least one beam is located. Alternatively, the source of radiation can be disposed within the chamber, thereby eliminating the requirement for a window or other transmissive means.

The chamber further has an interior surface, which may be curvilinear, rectilinear or combinations thereof. Furthermore, a portion or the entire interior surface may have various characteristics including highly reflective properties, surface undulations (linear or curvilinear) or features to assist in beam scattering or intended beam redirection. Moreover, the interior surface may be rigid or flexible. If flexible, the surface may be acted upon by a force (mechanical, electrical or pneumatic) to cause deflection thereof. In certain embodiments, the deflection is cyclical and characterized as a vibration.

The at least one beam of collimated electromagnetic radiation is characterized as having at least one discrete frequency or wavelength and preferably a plurality of wavelengths chosen to have particular efficacy at neutralizing the suspended micro-objects. The plurality of discrete wavelength ranges may be serially delivered to the chamber or may be simultaneously delivered. Neutralization includes destruction of the micro-object, functional disruption of the micro-object (as used herein, function disruption has particular applicability to rendering pathogens inactive or substantially biologically harmless), and vaporization of the micro-object. As used herein, "discrete wavelength" refers to a single wavelength and adjacent wavelengths within a small range thereof, e.g., those within about 1% of the primary wavelength.

The introduced at least one beam of collimated electromagnetic radiation can be a single beam of energy. In such an embodiment, the energy density of the beam can be diffused throughout the chamber by modifying the interior surface of the chamber to effect the desired beam diffusion or redirection. Alternatively, the introduced at least one beam of collimated electromagnetic radiation can be multiple beams of energy. In such an embodiment, a single beam is either divided into a plurality of beams prior to entering the chamber, with each beam having a unique angle of incidence when entering the chamber, or a single beam is optically redirected prior to entering the chamber such that each beam redirection results in the entering beam has a unique angle of incidence when entering the chamber. The former can be accomplished by passing the beam through a beam splitter or diffractive element, while the later can be accomplished by passing the beam through or reflecting the beam off a movable element. Alternative means for distributing the at least one beam include selectively removing the cladding from a fiber optic or periphery of a light pipe to permit partial escapement of any energy within the fiber or light pipe. Those persons skilled in the art will appreciate that the geometry of such material removal will create unique dispersion characteristics that may be matched to the particular environment in which the dispersion is desired.

The source of the at least one beam of collimated electromagnetic radiation is preferably a laser having a power output sufficient for achieving the intended purpose of the apparatus and methods. The laser may be of the continuous wave or pulsed type, with many preferred embodiments employing a pulsed type for reasons well known to those skilled in the art. Depending upon the energy density for a given application, a 10 watt $CO_2$ laser emitting radiation in the infrared region may be sufficient, or higher power and/or additional lasers may be employed. Again, the wavelength of the laser or ultimately emitted beam(s) is selected based upon the target species identified for neutralization.

The means for temporarily positioning an object in the chamber preferably comprises a substantially transparent platform for receiving the object, the degree of transparency being a function of the nature of the introduced electromagnetic radiation, e.g., its frequency and energy density. In this manner, the object to be sterilized is optically coupled to the at least one beam, and is subject to direct and/or reflected energy thereof. Alternative means for temporarily positioning an object in the chamber comprise substantially transparent clamps, tongs or other similar compressive devices. Note that the requirement for transparency only applies to those portions of the means that would otherwise interfere with the object's exposure to the beam.

To enhance the exposure of objects in the chamber to the radiation, the objects may be moved therein such as by carousel, conveyor, gantry, or other movable support platform. By moving objects in the chamber, portions of the objects that might otherwise be occluded from exposure thereto are repositioned to locations that optimize exposure. Moreover, by moving the objects through the exposure chamber, continuous process apparatus can be constructed where objects are introduced in one end and exit in a sterilized state at another end, much as with the air stream in the air sterilization apparatus.

While many embodiments of the object sterilization apparatus will use site-available power, this apparatus too can be modified to operate off grid. Therefore, alternative power sources for operation include a power generator utilizing an internal or external combustion engine to provide mechanical energy to a suitable electrical generator, a battery (rechargeable via, e.g., a solar array or not), or a fuel cell. For remote applications such sterilization operations in remote areas in third world countries, fuel cells provide a convenient and reliable means for providing the necessary power to operate even high power lasers; ubiquitously available methanol or ethanol can be used to power the apparatus.

Heretofore, the object sterilization apparatus comprised a chamber with only one sealable opening. However, certain applications may require mass object or continuous object sterilization operations. In such situations, the chamber can be modified to have a first opening and a second opening, and the means for temporarily positioning an object in the chamber comprises a movable conveyor portion utilizing a transparent belt or linked tread whereby objects can be introduced on the conveyor portion at the first opening and removed therefrom at the second opening. Because the object sterilization apparatus does not rely upon heat and/or pressure, the openings can be in communication with the external environment, with beam energy being attenuated by the use of an optical curtain that permits the conveyor and objects to exit the influence of the at least one beam prior to removal of the objects from the chamber. The conveyor portion may be motorized or hand operated, e.g., hand-wound torsion spring with escapement for moving conveyor portion. In an alternative arrangement, a "slide" is employed wherein the object to be sterilized is placed on an upper end of the slide via the first opening and permitted to move by the force of gravity to a lower end of the slide, which is proximate to the second opening of the chamber. During the transit, the object is exposed to the at least one beam and thereby sterilized. As with the previously described embodiments of this series, the slide is constructed of a material substantially transparent to the beam.

Applications for the object sterilization apparatus are primarily directed to those applications in which a hand tool or other similarly sized object is to undergo sterilization. Thus, reusable medical and dental instruments may be placed in the object sterilization apparatus and exposed to the at least one beam. After a predetermined time period (dependent upon the nature of the object placed in the apparatus), the object is removed from the apparatus in a sterilized state. A benefit of the object sterilization apparatus over that of a conventional autoclave is that there is no "warm up" period; the apparatus is instantly available for sterilization procedures. Another benefit is that the object can be removed very quickly from the apparatus after sterilization unlike an autoclave; the surface of the instrument either reflects the energy or very briefly may absorb a portion of the energy without appreciable heating of the instrument. Moreover, because of the limited duration for energy transfer to the instrument, instruments traditionally unsuitable for autoclave sterilization can be used and sterilized.

In still another series of embodiments, the at least one beam of collimated electromagnetic radiation is directed into a light pipe or fiber optic bundle of low attenuation material such as zinc selenide. Suitable dispersion features are created in the pipe or bundle so as to emit the radiation in at least a partially lateral direction. This probe embodiment find particular utility for sterilizing holly cylindrical bodies such as endoscopes and the like, where radiation would otherwise be prevented from entering for example, when exposed to the object sterilization apparatus.

DETAILED DESCRIPTION OF PREFERRED EMBODIMENTS

The following discussion is presented to enable a person skilled in the art to make and use the invention. Various modifications to the preferred embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein.

As described above, the invention is broadly characterized as a ported chamber into which at least one beam of collimated light energy is directed. The two embodiment series described below are functionally related. The air sterilization apparatus of FIGS. 1-2 have two openings for accepting air and delivering air while the object sterilization apparatus has only one, which is sealable. Furthermore, in the illustrated embodiments a 10 or 25 watt laser is used. The laser, sold by Synrad, Inc. under the "Series 48" designation, is a pulsed $CO_2$ laser emitting infrared collimated energy in the 10.60 micron range, and is FDA approved. Operational control of the laser (duty cycle and intermittent control) is preferably carried out by a personal computer operatively linked to the laser via a serial data cable interface provided on the lasers.

For embodiments requiring multiple wavelength light, any known means for shifting the native frequency or frequencies of the laser can be employed. Such shifting can be done sequentially over time (serial shifting), or the beam can be split and the resulting plurality of beams shifted as appropriate (parallel shifting). The selection of desired frequencies is dependent, in large part, upon the operational criteria of the apparatus, e.g., if the target of the sterilization process is biologic pathogens, then a certain suite of frequencies (wavelengths) are selected over other frequencies that are targeted to inorganic micro-objects. The selection of various wavelengths for each type of targeted micro-objects is well within the knowledge of those persons skilled in the art and will not be repeated here.

Figure 1:
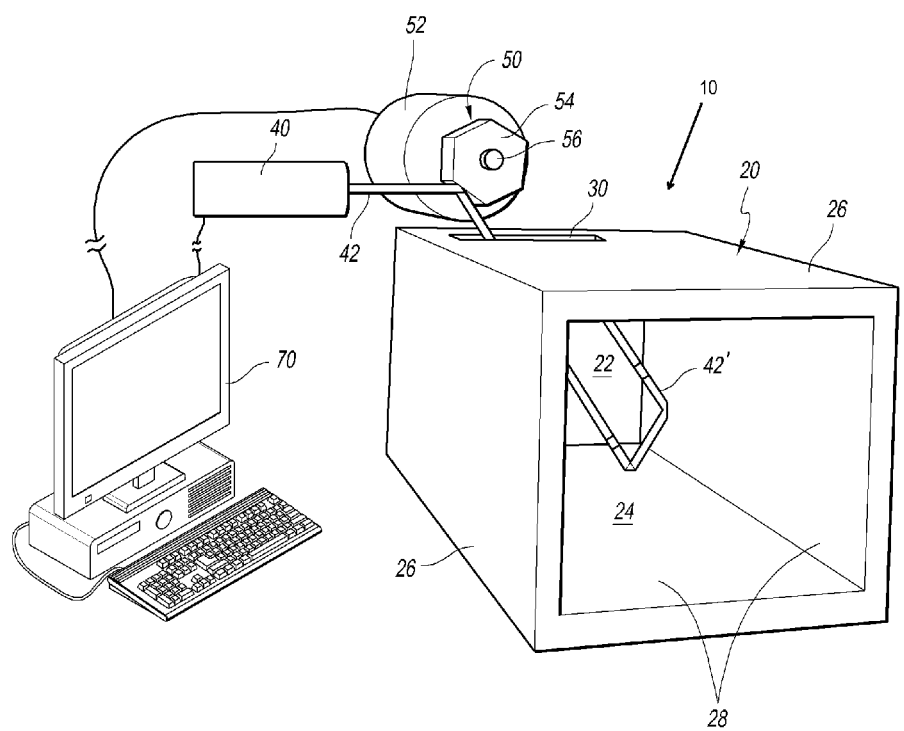
FIG. 1 is a schematic perspective view of a first air sterilization apparatus embodiment utilizing a rotating optic element to create numerous beams of energy in a chamber.

Turning then to FIG. 1, a first air sterilization apparatus embodiment utilizing a rotating optic element to create numerous beams of energy in a chamber is schematically shown. Apparatus 10 comprises chamber 20, which includes a plurality of exterior walls 26 that define first end 22 and second end 24 (thereby defining a longitudinal axis between these two ends) as well as window 30. Chamber 20 may be normal at all wall intersections or may be formed to diverge from first end 22 to second end 24, thus aiding in beam propagation. While not shown in this schematic representation, ends 22 and 24 are preferably adapted to integrate into the structure to which apparatus 10 is intended, as will be described below.

Interior walls 28 are preferably highly reflective of entering laser beam 42 so that beam 42 is repeatedly reflected within the volume defined by interior walls 28. The material used to achieve high reflectivity is chosen in view of the wavelength of the laser beam, however, surface treatments to interior walls 28 to facilitate propagation of the beam include forming linear and/or non-linear ridges and troughs at selected angles to the longitudinal dimension of the chamber; convex protrusions (faceted, smooth or combinations thereof); concave dimples (faceted, smooth or combinations thereof); regular protrusions and/or dimples; irregular protrusions and/or dimples; and smooth surfaces. The objective to surface treatments is to maximize at least one of the energy density within a particular volume within the chamber or total exposure time for any micro-object within the chamber as it traverses it.

FIG. 1 shows beam-type laser 40 directing beam 42 towards beam redirector 50. Beam redirector is shown schematically as comprising high speed stepper motor 52 to which optic element 54, constructed to include a suitable reflective material, is mounted via shaft 56. Redirected beam 42' then enters chamber 20 via transparent window 30, and repeatedly reflects within the interior of chamber 20. In operation, element 54 rotates so that a variety of entrance incident angles are created by beam 42', thereby distributing energy within chamber 20. To prevent errant reflection, controller 70 interfaces with laser 40 to switch it on and off in synchronicity with the operation of motor 52, which is also operatively linked to controller 70 in well known ways. In this manner, beam 42 is only presented to element 54 when redirected beam 42' is certain to pass through window 30. When coupled to a source of moving air, air entering first end 22 is exposed to laser beam energy prior to passing out of chamber 20 via second end 24.

Figure 2:
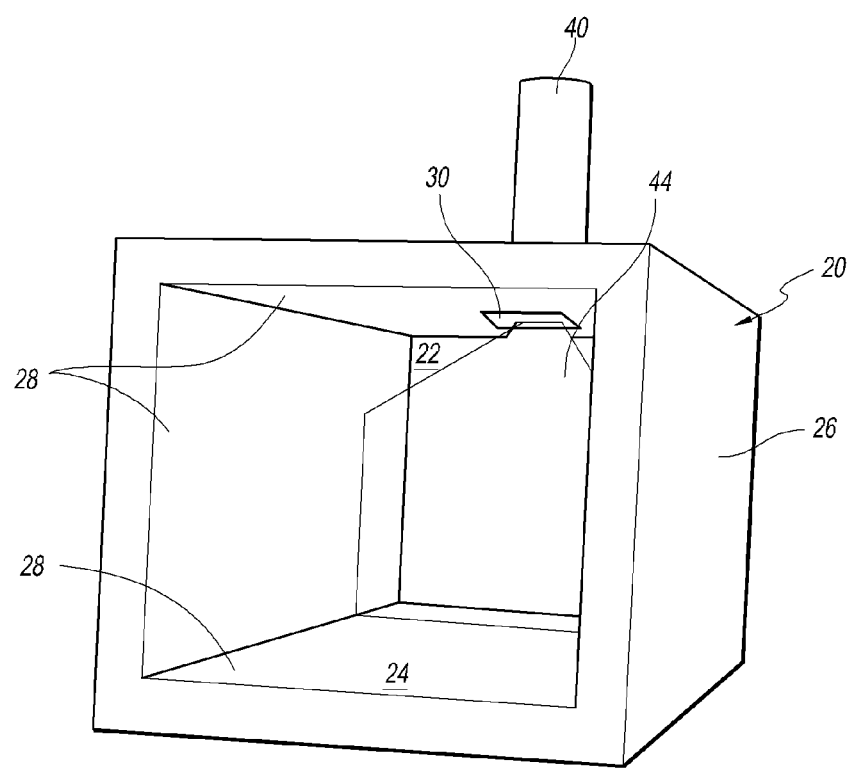
FIG. 2 is a schematic perspective view of a second air sterilization apparatus embodiment utilizing a beam diverging element to create a single "fan" of energy in a chamber.

In the event that a different dispersion pattern is desired, the configuration of the apparatus in FIG. 2 may be used. Chamber 20 remains essentially the same although the reflective properties of interior walls 28 may be modified in view of the unique variables introduced through the use of this embodiment. In this embodiment, a beam expanding or diverging element is used to create a line as opposed to a point. The result is a "fan" of beam energy 44, which is again reflected many times within the volume of chamber 20. While not shown in this embodiment, moving optics can be employed to cause movement of beam 44, although the nature of the beam decreases the need for a sweeping action, other factors being equal.

Figure 3:
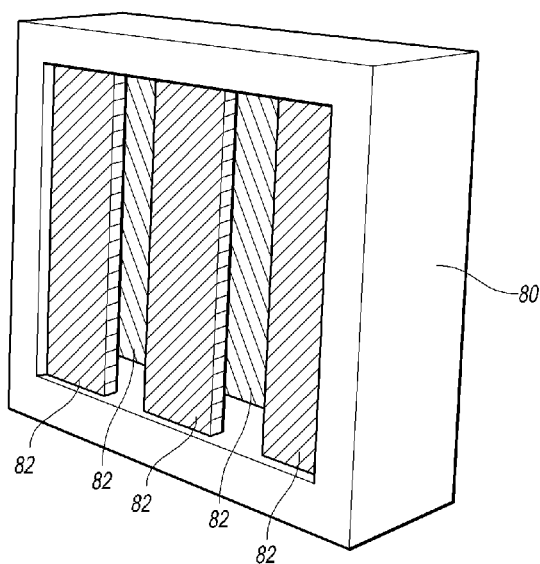
FIG. 3 is a perspective view of a light baffle to permit movement of air from one end thereof to another end, but attenuate laser energy.

To limit unintentional egress of beam energy from chamber 20, a pair of optic baffles such as shown in FIG. 3 may be used.

Housing 80 provides suitable support for a plurality of offset baffles 82, which permit air flow thereby but occlude any direct or indirect beam from exiting chamber 20. Baffles 82 can be constructed from any suitable material that absorbs and/or reflects beam energy. If the baffles absorb the energy, it may also be desirable to include means for cooling the baffles if the air flow rate is insufficient for the task.

Figure 4:
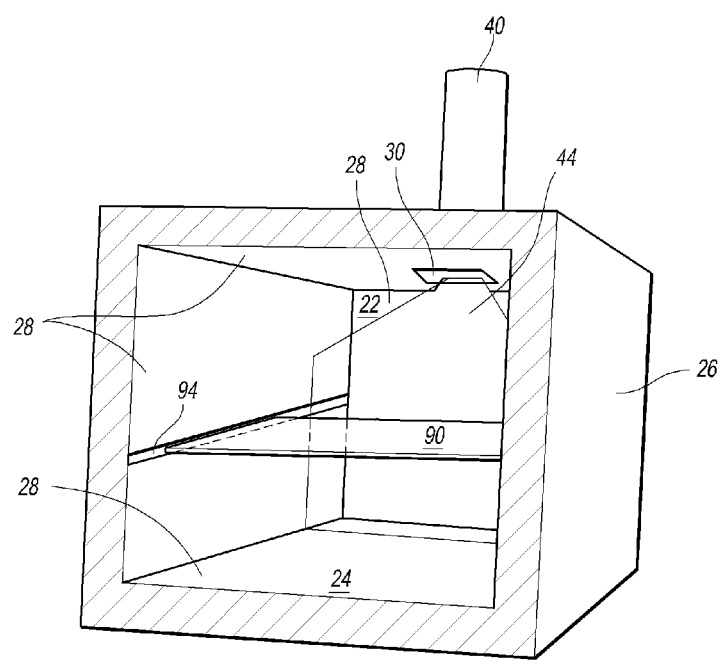
FIG. 4 is a schematic perspective view in cross section of an object sterilization apparatus embodiment utilizing a beam diverging element to create a single "fan" of energy in a chamber and a slidable transparent tray to receive objects to be sterilized.

FIG. 4 schematically illustrates the adaptation of the embodiment shown in FIG. 2 into an object sterilization apparatus. Here, first end 22 (shown in phantom) is closed and includes another interior wall 28. Tray 90 is supported by guides 94 present in opposing lateral walls 28. Optional mechanics translate tray 90 to provide maximum exposure of any object placed thereon to beam 44.

What is claimed is:

1. An air sterilization apparatus comprising:
    a chamber forming an interior volume comprising:
        a first end for introducing air into the chamber;
        a second end for permitting air to exit from the chamber;
        a transparent orifice through which a single beam of collimated light energy can be introduced into the interior volume of the chamber; and
        at least one reflective wall;
    a source for producing a single beam of collimated light energy;
    a motor; and
    a rotating beam redirector operatively connected to the motor, wherein the motor is configured to rotate the rotating beam director through a complete revolution about a rotational axis such that the rotating beam director redirects the single beam of collimated light energy within the chamber during said revolution.

2. The apparatus of claim 1, wherein the rotating beam redirector is configured such that the rotational axis is aligned approximately parallel with a longitudinal axis of the chamber, the longitudinal axis coinciding with the movement of air through the chamber between the first end and second end.

3. The apparatus of claim 1, wherein the rotating beam redirector and the chamber are positioned with respect to each other such that the single beam of collimated light energy is redirected within the chamber approximately orthogonal to a longitudinal axis of the chamber coinciding with the movement of air through the chamber between the first end and second end.

4. The apparatus of claim 1, wherein the rotating beam redirector comprises an optic element with a surface comprising a reflective material.

5. The apparatus of claim 1, wherein the rotating beam redirector comprises a beam diffractive element.

6. The apparatus of claim 1, wherein the rotating beam redirector is disposed between the transparent orifice and the source of collimated light energy.

7. The apparatus of claim 1, wherein the rotating beam redirector is disposed adjacent the transparent orifice and in the chamber.

8. The apparatus of claim 1 wherein the rotating beam redirector is positioned in the non-reflective interior surface portion of the chamber.

9. The apparatus of claim 1 wherein the rotating beam redirector does not oscillate around the rotational axis.

10. The apparatus of claim 1, wherein the transparent orifice comprises an optical window comprising a transparent material.

11. The apparatus of claim 1, wherein the chamber comprises at least one non-planar reflective wall.

12. The apparatus of claim 11, wherein the chamber is generally cylindrical.

13. The apparatus of claim 1, wherein the longitudinal cross-section of the chamber is approximately square-shaped.

14. The apparatus of claim 1, wherein the chamber further comprises a non-reflective interior surface comprising a material that absorbs the energy of the single beam of collimated light energy.

15. The apparatus of claim 1, wherein the collimated light energy is redirected prior to entering the chamber.

16. The apparatus of claim 1, wherein the source of collimated light energy is a laser.

17. The apparatus of claim 16, wherein the wavelength of light energy is in the infrared spectrum.

18. A system comprising the apparatus of claim 1 and an enclosure having a sealable interior environment and an environment control system comprising a duct for communicating air from a first location exposed to an exterior environment to a second location exposed to the interior environment where the first opening of the chamber is in communication with the exterior environment and the second opening is in communication with the interior environment.

19. The apparatus of claim 18 further comprising a self-contained power source for at least operation of the source of collimated light energy.

20. The apparatus of claim 1 further comprising a self-contained power source for at least operation of the source of collimated light energy.

21. The apparatus of claim 20 wherein the power source is one of a power generator, a battery, or a fuel cell.

22. An air sterilization apparatus comprising:
    a chamber forming an interior volume comprising:
        a first end for introducing air into the chamber;
        a second end for permitting air to exit from the chamber;
        a transparent orifice through which a single beam of collimated light energy can be introduced into the interior volume of the chamber; and
        at least one reflective wall;
    a source for producing a single beam of collimated light energy;
    a motor; and
    a beam redirector operatively connected to the motor and disposed to redirect the single beam of collimated light energy into a plurality of beams of collimated light energy across the interior of the chamber, the plurality of beams of collimated light energy aligned approximately orthogonally to a longitudinal axis of the chamber, the longitudinal axis coinciding with the movement of air through the chamber between the first end and second end.

23. The apparatus of claim 22, wherein the chamber comprises at least one non-planar reflective wall.

* * * * *